United States Patent
Pryma et al.

(10) Patent No.: US 10,457,642 B2
(45) Date of Patent: Oct. 29, 2019

(54) $^{211}$-ASTATINE CONTAINING RADIOTHERAPEUTICS FOR THE TREATMENT OF CANCER

(71) Applicant: The Trustees of The University of Pennsylvania, Philadelphia, PA (US)

(72) Inventors: Daniel A. Pryma, Bryn Mawr, PA (US); Brian P. Lieberman, Philadelphia, PA (US); Mehran Makvandi, Philadelphia, PA (US); Robert H. Mach, Wallingford, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/571,055

(22) PCT Filed: Apr. 26, 2016

(86) PCT No.: PCT/US2016/029289
§ 371 (c)(1),
(2) Date: Nov. 1, 2017

(87) PCT Pub. No.: WO2016/178852
PCT Pub. Date: Nov. 10, 2016

(65) Prior Publication Data
US 2018/0162818 A1    Jun. 14, 2018

Related U.S. Application Data

(60) Provisional application No. 62/156,534, filed on May 4, 2015.

(51) Int. Cl.
| | | |
|---|---|---|
| *A61K 51/00* | (2006.01) | |
| *A61K 9/00* | (2006.01) | |
| *A61K 41/00* | (2006.01) | |
| *C07D 217/04* | (2006.01) | |
| *G21H 5/02* | (2006.01) | |
| *A61K 51/04* | (2006.01) | |
| *C07D 209/44* | (2006.01) | |
| *A61K 45/06* | (2006.01) | |
| *A61P 35/00* | (2006.01) | |
| *A61N 5/10* | (2006.01) | |

(52) U.S. Cl.
CPC .......... *C07D 217/04* (2013.01); *A61K 9/0019* (2013.01); *A61K 41/0038* (2013.01); *A61K 45/06* (2013.01); *A61K 51/0446* (2013.01); *A61K 51/0455* (2013.01); *A61N 5/10* (2013.01); *A61P 35/00* (2018.01); *C07D 209/44* (2013.01); *G21H 5/02* (2013.01)

(58) Field of Classification Search
CPC ...... A61K 31/495; A61K 51/00; A61K 41/00; A61K 9/00
See application file for complete search history.

(56) References Cited

U.S. PATENT DOCUMENTS

| | | |
|---|---|---|
| 5,919,934 A | 7/1999 | John et al. |
| 7,390,902 B2 | 6/2008 | Mach et al. |
| 7,612,085 B2 | 11/2009 | Mach et al. |
| 7,612,206 B2 | 11/2009 | Mach et al. |
| 7,659,400 B2 | 2/2010 | Mach et al. |
| 7,893,266 B2 | 2/2011 | Mach et al. |
| 7,947,838 B2 | 5/2011 | Mach et al. |
| 8,143,222 B2 | 3/2012 | McDunn et al. |
| 8,168,650 B2 | 5/2012 | Mach et al. |
| 8,193,360 B2 | 6/2012 | Mach et al. |
| 8,329,686 B2 | 12/2012 | Mach et al. |
| 8,506,927 B2 | 8/2013 | Mach et al. |
| 8,658,131 B2 | 2/2014 | Tu et al. |
| 8,722,014 B2 | 5/2014 | Mach et al. |
| 8,735,575 B2 | 5/2014 | Zipfel et al. |
| 2005/0107398 A1* | 5/2005 | Mach ................. A61K 31/47 514/255.03 |
| 2008/0107599 A1 | 5/2008 | Mach et al. |

(Continued)

OTHER PUBLICATIONS

Francois Guerard Et al., Production of [211At]-Astatinated Radiopharmaceuticals and Applications in Targeted alpha-Particle Therapy, vol. 28(1), 1-20. (Year: 2013).*

Zeng C, Vangveravong S, Xu J, et al. Subcellular localization of sigma-2 receptors in breast cancer cells using two-photon and confocal microscopy. Cancer Research. 2007;67(14):6708-6716.

Zeng C, Vangveravong S, McDunn JE, Hawkins WG, Mach RH. Sigma-2 receptor ligand as a novel method for delivering a SMAC mimetic drug for treating ovarian cancer. British Journal of Cancer. 2013;109(9):2368-2377.

(Continued)

*Primary Examiner* — Michael G. Hartley
*Assistant Examiner* — Jagadishwar R Samala
(74) *Attorney, Agent, or Firm* — BakerHostetler

(57) ABSTRACT

Described herein is an alpha-emitting radionuclide, $^{211}$At, which has been incorporated into a selective sigma-2 ligand moiety to provide cytotoxic capabilities to a chemical compound. As described herein, a compound of formula (I), wherein $R^1$-$R^4$, m, and n are defined herein, was prepared and utilized in in vitro and in vivo tumor targeting of alpha-emitting sigma-2 ligand in a breast cancer model. In one embodiment, the compound is 5-($^{211}$At)—N-(4-(6,7-dimethoxy-3,4-dihydroisoquinolin-2(1H)-yl)butyl)-2,3-dimethoxybenzamide.

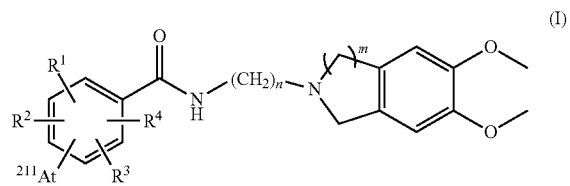

23 Claims, 6 Drawing Sheets

(56) References Cited

U.S. PATENT DOCUMENTS

| | | |
|---|---|---|
| 2008/0161343 A1 | 7/2008 | Mach et al. |
| 2009/0068105 A1 | 3/2009 | Mach et al. |
| 2009/0176705 A1 | 7/2009 | McDunn et al. |
| 2010/0028936 A1 | 2/2010 | Mach et al. |
| 2010/0048614 A1 | 2/2010 | Mach et al. |
| 2010/0150836 A1 | 6/2010 | Mach et al. |
| 2010/0278732 A1 | 11/2010 | Mach et al. |
| 2010/0278751 A1 | 11/2010 | Mach et al. |
| 2011/0230662 A1 | 9/2011 | Mach et al. |
| 2011/0311447 A1 | 12/2011 | Tu et al. |
| 2012/0035359 A1 | 2/2012 | Zipfel et al. |
| 2012/0100073 A1 | 4/2012 | Mach et al. |
| 2012/0171119 A1 | 7/2012 | Mach et al. |
| 2013/0079522 A1 | 3/2013 | Mach et al. |
| 2013/0315825 A1 | 11/2013 | Tu et al. |
| 2014/0378460 A1 | 12/2014 | Catalano et al. |

OTHER PUBLICATIONS

Zeng C, Rothfuss JM, Zhang J, et al. Functional assays to define agonists and antagonists of the sigma-2 receptor. Analytical Biochemistry. 2014;448:68-74.

Zeng C, Rothfuss J, Zhang J, et al. Sigma-2 ligands induce tumour cell death by multiple signalling pathways. British Journal of Cancer. 2012;106(4):693-701.

Zalutsky MR, Zhao XG, Alston KL, Bigner D. High-level production of alphaparticle-emitting (211)At and preparation of (211)At-labeled antibodies for clinical use. Journal of nuclear medicine : official publication, Society of Nuclear Medicine. 2001;42(10):1508-1515.

Xu J, Zeng C, Chu W, et al. Identification of the PGRMC1 protein complex as the putative sigma-2 receptor binding site. Nature Communications. 2011;2:380.

Wilbur DS. [211At]Astatine-Labeled Compound Stability: Issues with Released [211At]Astatide and Development of Labeling Reagents to Increase Stability. Current Radiopharmaceuticals. 2008(1):144-176.

Wheeler KT, Wang LM, Wallen CA, et al. Sigma-2 receptors as a biomarker of proliferation in solid tumours. British Journal of Cancer. 2000;82(6):1223-1232.

Vangveravong S, Xu J, Zeng C, Mach RH. Synthesis of N-substituted 9-azabicyclo[3.3.1]nonan-3alpha-yl carbamate analogs as sigma2 receptor ligands. Bioorganic & Medicinal Chemistry. 2006;14(20):6988-6997.

Van Waarde A, Rybczynska AA, Ramakrishnan NK, Ishiwata K, Elsinga PH, Dierckx RA. Potential applications for sigma receptor ligands in cancer diagnosis and therapy. Biochimica et Biophysica Acta. 2014:2703-2714.

Tu, "Fluorine-18-labeled bensamide analogues for imaging the sigma-2 receptor status of solid tumors with positron emission tomography", Journal of Medicinal Chemistry. 2007;50(14):3194-3204.

Tu Z, Dence CS, Ponde DE, et al. Carbon-11 labeled sigma2 receptor ligands for imaging breast cancer. Nuclear Medicine and Biology. 2005;32(5):423-430.

Testa et al., "Prodrugs Revisited: The "Ad Hoc" Approach as a complement to Ligand Design", Medicinal Reviews, 16 (3), 233-241, ed., John Wiley & Sons, 1996.

Spitzer D, Simon PO, Jr., Kashiwagi H, et al. Use of multifunctional sigma-2 receptor ligand conjugates to trigger cancer-selective cell death signaling. Cancer Research. 2012;72(1):201-209.

Spetz J, Rudqvist N, Forssell-Aronsson E. Biodistribution and dosimetry of free 211At, 125I- and 131I-in rats. Cancer Biotherapy & Radiopharmaceuticals. 2013;28(9):657-664.

Parker C, Nilsson S, Heinrich D, et al. Alpha emitter radium-223 and survival in metastatic prostate cancer. The New England Journal of Medicine. 2013;369(3):213-223.

Mach RH, Zeng C, Hawkins WG. The sigma2 receptor: a novel protein for the imaging and treatment of cancer. Journal of Medicinal Chemistry. 2013;56(18):7137-7160.

Mach RH, Smith CR, al-Nabulsi I, Whirrett BR, Childers SR, Wheeler KT. Sigma 2 receptors as potential biomarkers of proliferation in breast cancer. Cancer Research. 1997;57(1):156-161.

Mach RH, Huang Y, Freeman RA, Wu L, Vangveravong S, Luedtke RR. Conformationally-flexible benzamide analogues as dopamine D3 and sigma 2 receptor ligands. Bioorganic & Medicinal Chemistry Letters. 2004;14 (1)195-202.

Mach RH, Huang Y, Buchheimer N, et al. [(18)F]N-(4'-fluorobenzyl)-4-(3-bromophenyl) acetamide for imaging the sigma receptor status of tumors: comparison with [(18)F]FDG, and [(125)I]UDR. Nuclear Medicine and Biology. 2001;28(4):451-458.

Kennel SJ, Stabin M, Roeske JC, et al. Radiotoxicity of bismuth-213 bound to membranes of monolayer and spheroid cultures of tumor cells. Radiation Research. 1999;151(3):244-256.

Kashiwagi H, McDunn JE, Simon PO, Jr., et al. Sigma-2 receptor ligands potentiate conventional chemotherapies and improve survival in models of pancreatic adenocarcinoma. Journal of Translational Medicine. 2009;7:24.

Kashiwagi H, McDunn JE, Simon PO, Jr., et al. Selective sigma-2 ligands preferentially bind to pancreatic adenocarcinomas: applications in diagnostic imaging and therapy. Molecular Cancer. 2007;6:48.

Jurcic JG, Rosenblat TL. Targeted alpha-particle immunotherapy for acute myeloid leukemia. American Society of Clinical Oncology educational book /ASCO. American Society of Clinical Oncology. Meeting. 2014:e126-131.

John CS, Vilner BJ, Bowen WD. Synthesis and characterization of [125I]-N-(Nbenzylpiperidin-4-yl)-4-iodobenzamide, a new sigma receptor radiopharmaceutical: high-affinity binding to MCF-7 breast tumor cells. Journal of Medicinal Chemistry. 1994;37(12):1737-1739.

Hou, "Characterization of a novel iodinated sigma-2 receptor ligand as a cell proliferation marker", Nuclear Medicine and Biology. 2006;33(2):203-209.

Hornick JR, Xu J, Vangveravong S, et al. The novel sigma-2 receptor ligand SW43 stabilizes pancreas cancer progression in combination with gemcitabine. Molecular Cancer. 2010;9:298.

Hellewell SB, Bruce A, Feinstein G, Orringer J, Williams W, Bowen WD. Rat liver and kidney contain high densities of sigma 1 and sigma 2 receptors: characterization by ligand binding a and photoaffinity labeling. European Journal of Pharmacology. 1994;268(1):9-18.

Hashim YM, Spitzer D, Vangveravong S, et al. Targeted pancreatic cancer therapy with the small molecule drug conjugate SW IV-134. Molecular Oncology. 2014;8(5):956-967.

Guerard F, Gestin JF, Brechbiel MW. Production of [(211)At]-astatinated radiopharmaceuticals and applications i targeted alpha-particle therapy. Cancer Biotherapy & Radiopharmaceuticals. 2013;28(1):1-20.

Garg G, Vangveravong S, Zeng C, et al. Conjugation to a SMAC mimetic potentiates sigma-2 ligand induced tumor cell death in ovarian cancer. Molecular Cancer. 2014;13:50.

Fan et al. 'Effect of structural modification in the amine portion of substituted aminobutylbenzamides as ligands for binding sigma1 and sigma2 receptors', Bioorg Med Chem. 2011;19(6):1852-1859.

Dehdashti F, Laforest R, Gao F, et al. Assessment of cellular proliferation in tumors by PET using 18F-ISO-1. Journal of nuclear medicine : official publication, Society of Nuclear Medicine. 2013;54(3):350-357.

Chu W, Xu J, Zhou D, et al. New N-substituted 9-azabicyclo[3.3.1]nonan-3alphayl phenylcarbamate analogs as sigma2 receptor ligands: synthesis, in vitro characterization, and evaluation as PET imaging and chemosensitization agents. Bioorganic & Medicinal Chemistry. 2009;17(3):1222-1231.

Bem WT, Thomas GE, Mamone JY, et al. Overexpression of sigma receptors in nonneural human tumors. Cancer Research. 1991;51(24):6558-6562.

Al-Nabulsi I, Mach RH, Wang LM, et al. Effect of ploidy, recruitment, environmental factors, and tamoxifen treatment on the expression of sigma-2 receptors in proliferating and quiescent tumour cells. British Journal of Cancer. 1999;81 (6):925-933.

\* cited by examiner

1. Vacuum Outlet
2. Charcoal Traps
3. Liquid Vacuum Trap
4. Dose Calibrator
5. Liquid NaOH Trap
6. Furnace
7. Quartz Furnace Tube
8. Solid Target
9. Vent
10. Argon Inlet

211-ASTATINE CONTAINING RADIOTHERAPEUTICS FOR THE TREATMENT OF CANCER

CROSS-REFERENCE TO RELATED APPLICATIONS

This application is the National Stage Application of International Patent Application No. PCT/US2016/029289, filed Apr. 26, 2016, which claims the benefit of the priority of U.S. Provisional Patent Application No. 62/156,534, filed May 4, 2015, both applications of which are incorporated by reference.

STATEMENT REGARDING FEDERALLY SPONSORED RESEARCH

This invention was made with Government support under Grant Number DE-SE0012476 awarded by the Department of Energy. The Government has certain rights in the invention.

TECHNICAL FIELD

This invention relates to the field of $^{211}$-astatine containing radiotherapeutics for treating cancer.

BACKGROUND

The sigma-2 receptor is a promising target for cancer therapy due to its overexpression in multiple malignancies including: breast, pancreatic, ovarian, lung, renal, melanoma, neuroendocrine and colon. The molecular function of the sigma-2 receptor has been defined through pharmacological studies that have validated it as a biomarker that can be utilized to non-invasively measure the proliferative status of tumors. During cell proliferation the sigma-2 receptor is overexpressed by a factor of 10 compared with quiescent or nonproliferative cells. Confocal microscopy studies have shown the subcellular localization of sigma-2 receptors on cell membrane, lysosomes, endoplasmic reticulum, and mitochondria.

Sigma-2 ligands, classified as azabicyclononane derivatives, have been shown to undergo rapid internalization and are capable of inducing caspase dependent and independent cell death pathways. More recently, the molecular identity of the sigma-2 receptor was identified as the progesterone receptor membrane component 1 (PGRMC1), providing new insight and potential for further defining its biological, pharmacological and molecular properties. Three classes of sigma-2 ligands have been characterized pharmacologically through caspase-3/7 activation as agonist, partial agonist or antagonist. Azabicyclononane and tropane analogs induce or partially induce downstream caspase 3/7 activation, and therefore are considered agonist to the sigma-2 receptor. The benzamide class of ligands acts as antagonists, unable to induce caspase activity, and is believed to interact with binding sites on the surface membranes, although passive diffusion across the cell membrane has not been evaluated.

Sigma-2 antagonists have been historically developed as imaging agents due to their safe toxicity profile and high affinity and selectivity for the sigma-2 receptor, as well as fast tumor targeting and clearance in vivo. Numerous selective sigma-2 ligands have been reported, however, N-(4-(6, 7-dimethoxy-3,4-dihydroisoquinolin-2(1H)-yl)butyl)-2-(2-F-fluoromethoxy)-5-methylbenzamide is the only diagnostic imaging agent used clinically in a research setting. Other sigma-2 ligands have been applied in chemosensitization and the targeted delivery of cancer therapeutics showing a beneficial therapeutic response in pre-clinical models. Currently, only sigma-2 agonist conjugates have been used as therapeutics. This has been most likely due to the lack of cytotoxicity observed with sigma-2 antagonists and evidence to support whether this class of ligands enters the cell, which is an important characteristic for the therapeutics ability to reach the site of action.

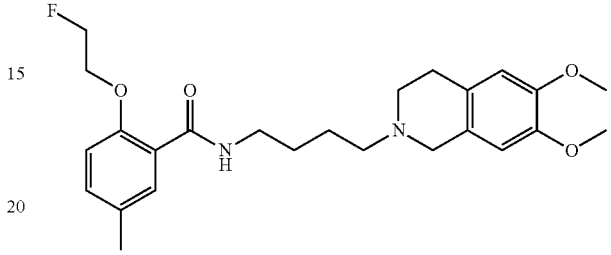

N-(4-(6,7-dimethoxy-3,4-dihydroisoquinolin-2(1H)-yl)butyl)-2-(2-F-fluoroethoxy)-5-methylbenzamide What are needed in the art are alternate chemotherapeutics for treating cancer.

SUMMARY OF THE INVENTION

In one aspect, a compound having the structure of formula (I), or a pharmaceutically acceptable salt or prodrug thereof, is provided, wherein $R^1$-$R^4$, n, and m are defined herein.

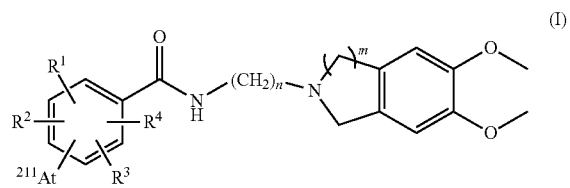

In another aspect, the compound has the structure of formula (II), or a pharmaceutically acceptable salt or prodrug thereof, is provided, wherein $R^1$-$R^4$, n, and m are defined herein.

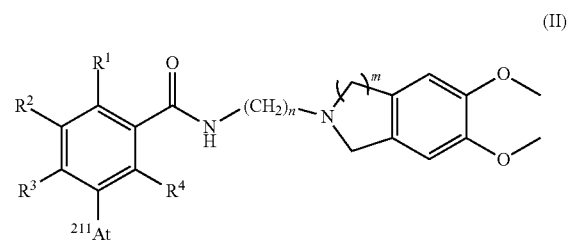

In a further aspect, the compound has the structure of formula (III), (IV), (V), (VI), (VII), or (VIII):

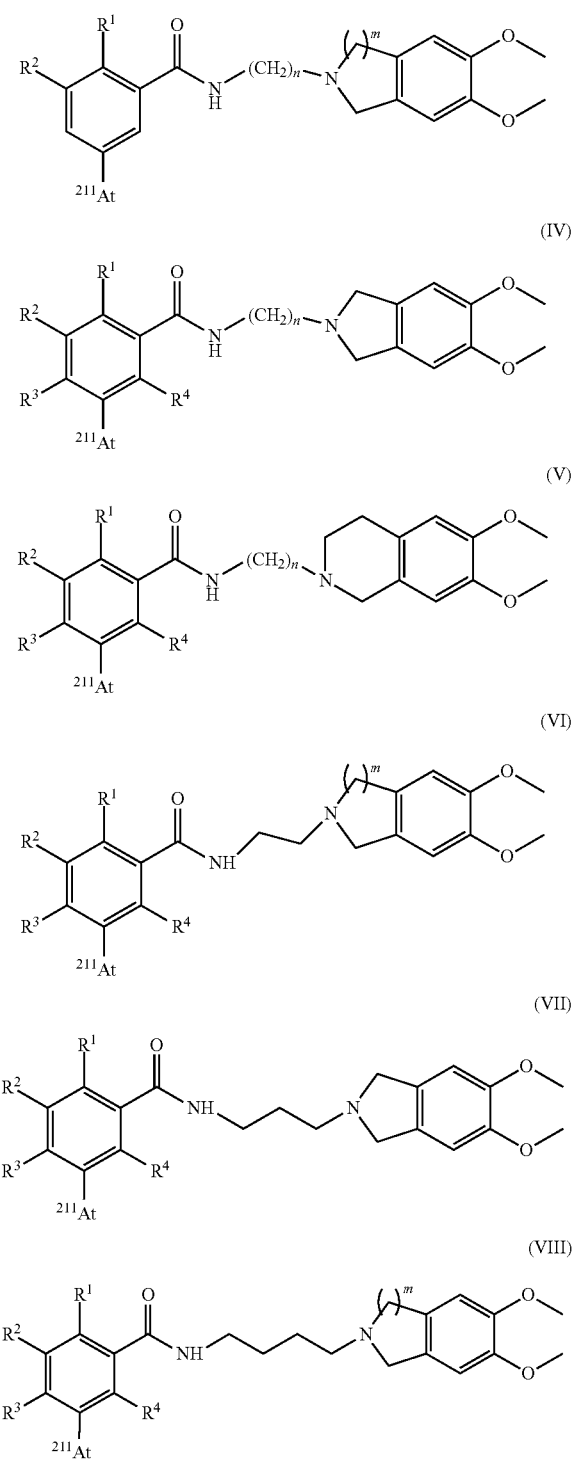

In yet another aspect, 5-($^{211}$astatine)-N-(4-(6,7-dimethoxy-3,4-dihydroisoquinolin-2(1H)-yl)butyl)-2,3-dimethoxybenzamide, derivative, salt, or prodrug thereof is provided.

In still a further aspect, a composition is provided and contains a compound described herein and a pharmaceutically acceptable carrier or diluent.

In another embodiment, a method of preventing or reducing proliferation of cancer cells is provided and includes contacting the cells with a compound or composition described herein.

In a further aspect, a method of sensitizing cancer cells to a chemotherapeutic is provided and includes comprising contacting the cells with a compound or composition described herein.

In still another aspect, a method of modulating expression of the sigma-2-receptor/progesterone receptor membrane component 1 on a cell is provided and includes contacting the cell with a compound or composition described herein.

In yet a further aspect, a method of treating cancer in a patient is provided and includes administering a compound or composition described herein to the patient.

In another aspect, a method of administering radiotherapy to a patient in need thereof is provided and includes administering a compound or composition described herein to the patient.

Other aspects and embodiments of the invention will be readily apparent from the following detailed description of the invention.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific compositions, methods, devices, and systems disclosed. In addition, the drawings are not necessarily drawn to scale.

DETAILED DESCRIPTION OF THE INVENTION

Figure 1:
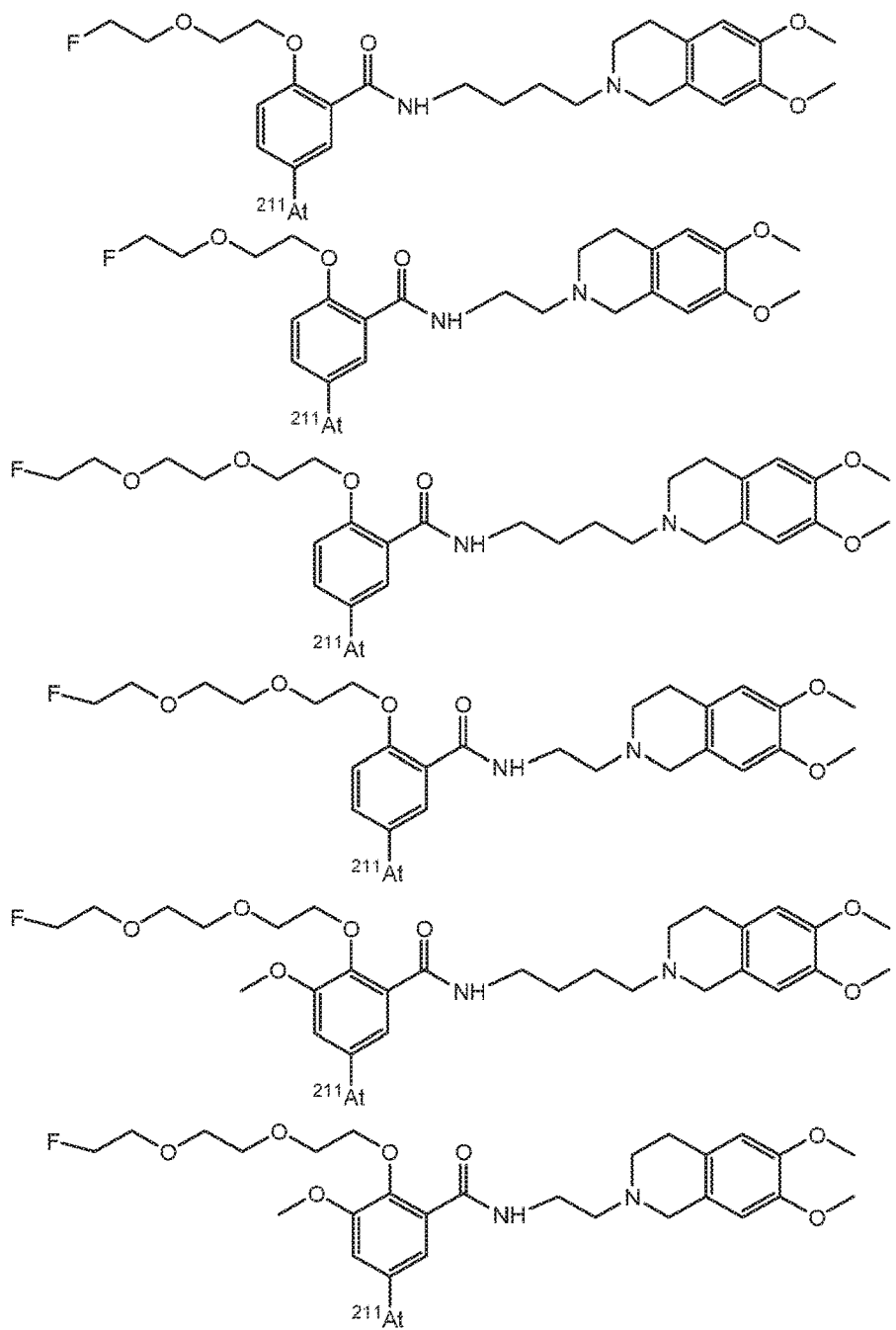
FIG. 1 are examples of $^{211}$At-containing compounds encompassed by the structure of formula (I).
Figure 1:
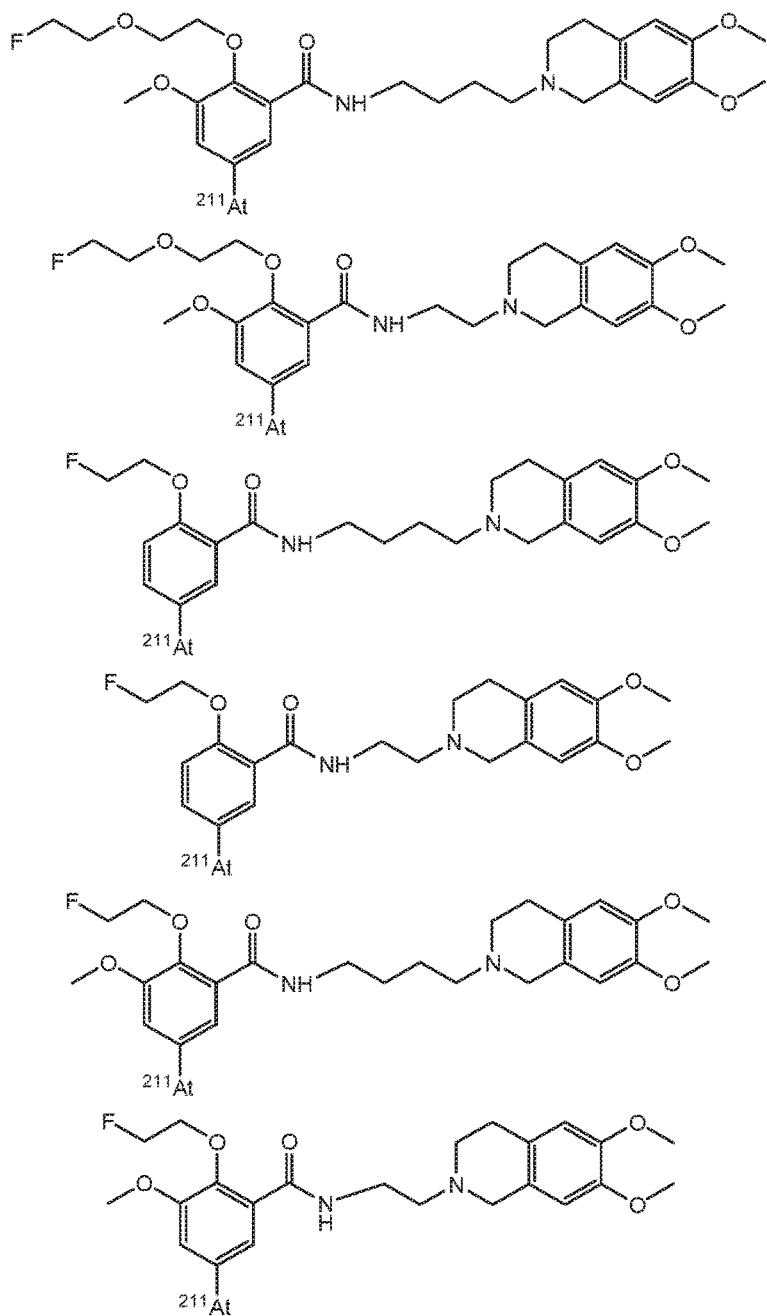
Figure 1:
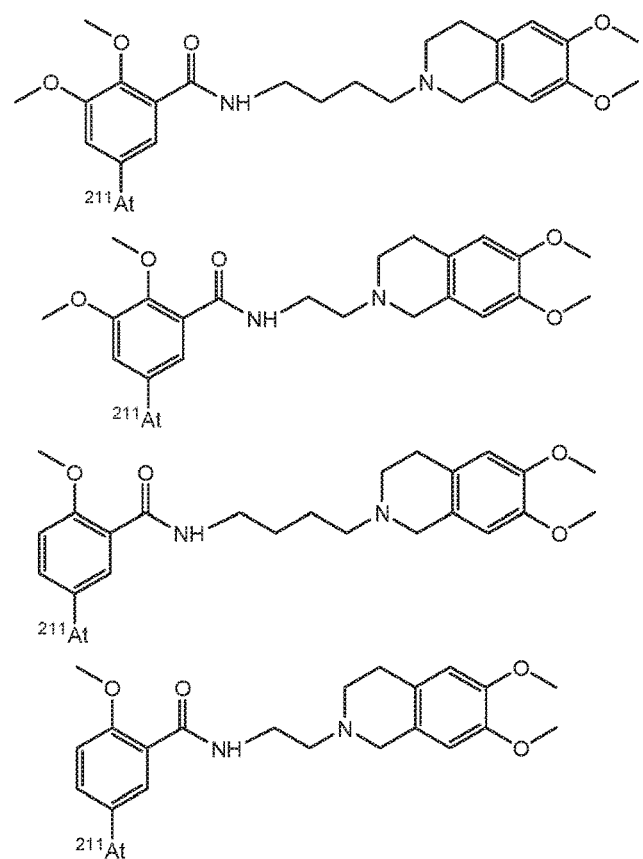

In the present disclosure the singular forms "a", "an" and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" or "substantially" it will be understood that the particular value forms another embodiment. In general, use of the term "about" or "substantially" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about" or "substantially". In other cases, the gradations used in a series of values may be used to determine the intended range available to the term "about" or "substantially" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

Alpha-emitting radionuclides have the potential for new therapeutic drug development and can result in new treatments for clinical utilization to combat cancer.

I. The Compounds $^{211}$Astatine ($^{211}$At) is a radionuclide that decays through the emission of a high-energy alpha particle and has a half-life of 7.21 h. Alpha-particles travel approximately 2-3 cell diameters (50-100 μm) and cause dense ionizations along the track resulting in clustered DNA damage capable of inducing cell death. The short path-length of an alpha particle also translates to a highly specific cell killing capability. Cells only within immediate proximity to the radioactive decay event are affected. It is hypothesized that as few as 10 alpha-particles traversing a cell have a high probability of inducing cell death.

The compounds discussed herein are alpha-emitting radionuclides. The compounds modulate expression of the sigma-2-receptor/progesterone receptor membrane component 1 on a cell and are, thereby, effective in treating conditions, i.e., cancer, associated with the same. The compounds discussed herein contain a $^{211}$At group as a substituent of the molecule. Such compounds are anticipated to be highly effective in treating a number of conditions which require applying internal radiation to a patient. In one embodiment, the compounds discussed herein may have a high therapeutic index. In another embodiment, the compounds have the potential to overcome resistance pathways through direct tumoricidal DNA damage. Accordingly, the compounds discussed herein have use as a radiopharmaceutical. Advantageously, it is anticipated that the cost of $^{211}$At and compounds containing same will be less than the cost of commercially available, radioactive $^{123}$I.

The compounds discussed herein have the structure of formula (I) or a pharmaceutically acceptable salt or prodrug thereof.

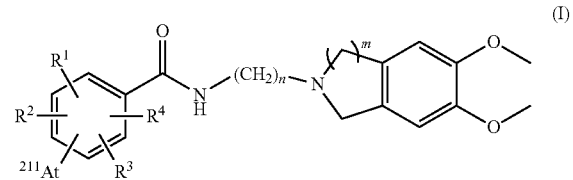

(I)

In this structure, m is 1 or 2 and n is 1 to 10. In one embodiment, n is 2 to 4.

$R^1$ to $R^4$ are attached to the benzene ring at carbon-atoms the 2-, 3-, 4-, 5-, or 6-position. $R^1$ to $R^4$, independently, occupy any position of the benzene ring, with the proviso that two of $R^1$-$R^4$ and $^{211}$At do not occupy the same position on the benzene ring. $R^1$ to $R^4$ are, independently, H, $C_1$ to $C_6$ alkyl, $C_1$ to $C_6$ alkoxy, $C_1$ to $C_6$ haloalkyl, halogen, $C_1$ to $C_6$ fluoroalkoxy, $C_1$ to $C_6$ thioalkyl, $C_1$ to $C_6$ thio-haloalkyl, $NH_2$, $C_1$ to $C_6$ aminoalkyl, or —$(OCH_2CH_2)_q$—F and q is 2 to 6. In one embodiment, $R^1$ is $C_1$ to $C_6$ fluoroalkoxy. In another embodiment, $R^1$ is —$O(CH_2)_p$F and p is 1 to 10. In a further embodiment, the halogen is a radioactive isotope.

Alternatively, any two of $R^1$ to $R^4$ together may form a 5- or 6-membered benzene ring. In one embodiment, $R^1$ and $R^2$; $R^2$ and $R^3$; or $R^3$ and $R^4$ together form a 5- or 6-membered benzene ring. This benzene ring may be substituted with H or 1 to 4 $R^5$. $R^5$ is H, $C_1$ to $C_6$ alkyl, $C_1$ to $C_6$ alkoxy, $C_1$ to $C_6$ haloalkyl, halogen, $C_1$ to $C_6$ fluoroalkoxy, $C_1$ to $C_6$ thioalkyl, $C_1$ to $C_6$ thio-haloalkyl, $NH_2$, $C_1$ to $C_6$ aminoalkyl, or —$(OCH_2CH_2)_q$—F, where q is defined above. In one embodiment, the halogen is a radioactive isotope.

The $^{211}$At substituent may be any position, i.e., the 2-, 3-, 4-, 5- or 6-position, of the benzene ring. In one embodiment, the $^{211}$At is 3-position of the benzene ring.

In one embodiment, the compound has the structure of formula (II), wherein $R^1$-$R^4$, m, and n are defined herein.

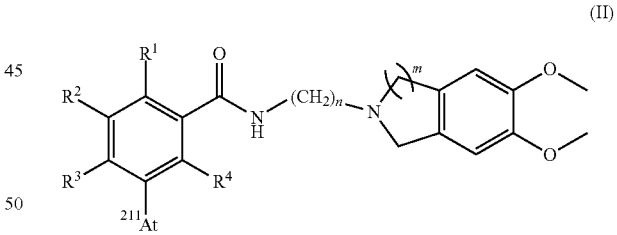

(II)

In another embodiment, the compound has the structure of formula (III), wherein $R^1$, $R^2$, m, and n are defined herein.

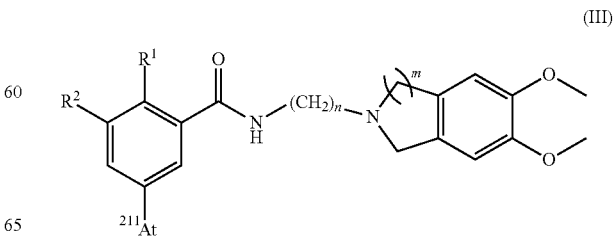

(III)

In a further embodiment, the compound has the structure of formula (IV), wherein $R^1$-$R^4$ and n are defined herein.

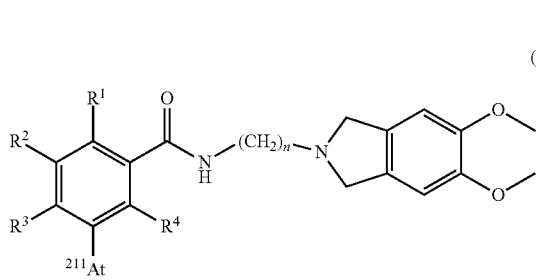

(IV)

In yet another embodiment, the compound has the structure of formula (V), wherein $R^1$-$R^4$ and n are defined herein.

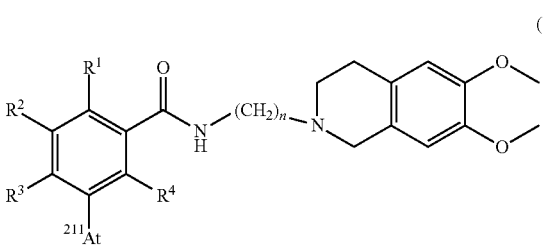

(V)

In still a further embodiment, the compound has the structure of formula (VI), wherein $R^1$-$R^4$ and m are defined herein.

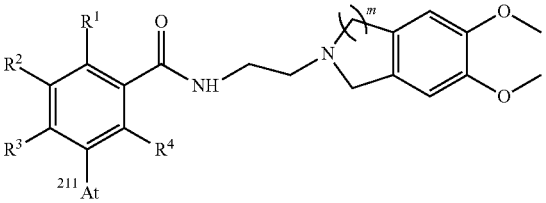

(VI)

In another embodiment, the compound has the structure of formula (VII), wherein $R^1$-$R^4$ are defined herein.

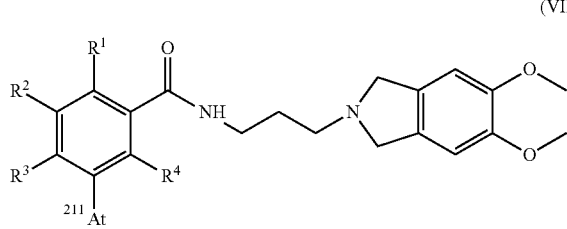

(VII)

In a further embodiment, the compound has the structure of formula (VIII), wherein $R^1$-$R^4$ and m are defined herein.

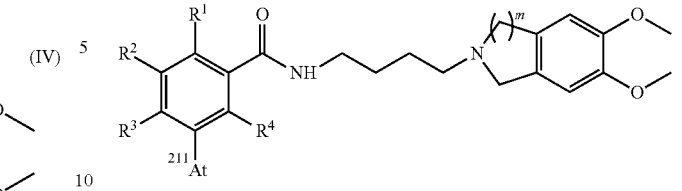

(VIII)

In still another embodiment, the compound is a compound set forth in FIG. 1, or a derivative, salt, or prodrug thereof.

In yet a further embodiment, the compound is 5-($^{211}$astatine)-N-(4-(6,7-dimethoxy-3,4-dihydroisoquinolin-2(1H)-yl)butyl)-2,3-dimethoxybenzamide, derivative, salt, or prodrug thereof.

The term "alkyl" is used herein to refer to both straight- and branched-chain saturated aliphatic hydrocarbon groups. In one embodiment, an alkyl group has 1 to about 10 carbon atoms. In another embodiment, an alkyl group has 1 to about 6 carbon atoms. In a further embodiment, an alkyl group has 1 to about 4 carbon atoms.

The term "alkoxy" as used herein refers to the O-(alkyl) group, where the point of attachment is through the oxygen-atom and the alkyl group is defined above.

The term "thioalkyl" as used herein refers to the S-(alkyl) group, where the point of attachment is through the sulfur-atom and the alkyl group is defined above.

The term "aminoalkyl" as used herein refers to both secondary and tertiary amines where the point of attachment is through the nitrogen-atom and the alkyl groups are defined above. The alkyl groups can be the same or different.

The term "halogen" as used herein refers to Cl, Br, F, or I groups.

The term "haloalkyl" as used herein refers to an alkyl group that is substituted at one or more carbon atom of the alkyl chain with a halogen group. The point of attachment of the haloalkyl is through a carbon atom of the alkyl chain.

The term "fluoroalkoxy" as used herein refers to an alkoxy group that is substituted at one or more carbon atom of the alkyl chain with a fluorine atom. The point of attachment of the fluoroalkoxy is through a carbon atom of the alkoxy chain.

The term "thio-haloalkyl" as used herein refers to the —S(haloalkyl) group, where the point of attachment is through the sulfur-atom and the haloalkyl group is defined above.

II. Methods of Production

The compounds described above may be prepared by known chemical synthesis techniques. These compounds may also be purchased from commercial vendors, e.g., the Sigma-Aldrich Co. Among such preferred techniques known to one of skill in the art are included the synthetic methods described in conventional textbooks relating to the construction of synthetic compounds.

In one embodiment, $^{211}$At is prepared as described by irradiation of a $^{209}$bismuth target in a cyclotron through the nuclear reaction Bi-209(α, 2n)At-211 as described below. In one embodiment, the cyclotron produce alpha beams at energies of about 28.5 MeV. In one embodiment, the cyclotrons and/or systems utilized to prepare the $^{211}$At or the compounds described herein would be readily accessible to a facility for treating a patient. In another embodiment, the systems and/or cyclotrons are located no more than about 24 hours from a facility for treating a patient with the compounds discussed herein. In a further embodiment, the systems and/or cyclotrons are located no more than about 12 hours from a facility for treating a patient with the compounds discussed herein. In yet another embodiment, the systems and/or cyclotrons are located no more than about 8 hours from a facility for treating a patient with the compounds discussed herein. In still a further embodiment, the systems and/or cyclotrons are located no more than about 4 hours from a facility for treating a patient with the compounds discussed herein.

III. Compositions Containing the Compound

Pharmaceutical compositions useful herein, in one embodiment, contain a compound discussed above in a pharmaceutically acceptable carrier or diluent with other optional suitable pharmaceutically inert or inactive ingredients. In another embodiment, a compound described above is present in a single composition. In a further embodiment, a compound described above is combined with one or more excipients and/or other therapeutic agents as described below.

(i) Salts

The compounds discussed above may encompass tautomeric forms of the structures provided herein characterized by the bioactivity of the drawn structures. Further, the compounds may also be used in the form of salts derived from pharmaceutically or physiologically acceptable acids, bases, alkali metals and alkaline earth metals.

In one embodiment, pharmaceutically acceptable salts can be formed from organic and inorganic acids including, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

In another embodiment, pharmaceutically acceptable salts may also be formed from inorganic bases, desirably alkali metal salts including, e.g., sodium, lithium, or potassium, such as alkali metal hydroxides. Examples of inorganic bases include, without limitation, sodium hydroxide, potassium hydroxide, calcium hydroxide, and magnesium hydroxide. Pharmaceutically acceptable salts may also be formed from organic bases, such as ammonium salts, mono-, di-, and trimethylammonium, mono-, di- and triethylammonium, mono-, di- and tripropylammonium, ethyldimethylammonium, benzyldimethylammonium, cyclohexylammonium, benzyl-ammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1 n-butyl piperidinium, 2-methylpiperidinium, 1-ethyl-2-methylpiperidinium, mono-, di- and triethanolammonium, ethyl diethanolammonium, n-butylmonoethanolammonium, tris (hydroxymethyl)methylammonium, phenylmono-ethanolammonium, diethanolamine, ethylenediamine, and the like. In one example, the base is selected from among sodium hydroxide, lithium hydroxide, potassium hydroxide, and mixtures thereof.

(ii) Prodrugs

The salts, as well as other compounds, can be in the form of esters, carbamates and other conventional "pro-drug" forms, which, when administered in such form, convert to the active moiety in vivo. In one embodiment, the prodrugs are esters. In another embodiment, the prodrugs are carbamates. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996), which is incorporated by reference.

(iii) Carriers and Diluents

The pharmaceutical compositions include a compound described herein formulated neat or with one or more pharmaceutical carriers for administration, the proportion of which is determined by the solubility and chemical nature of the compound, chosen route of administration and standard pharmacological practice. The pharmaceutical carrier may be solid or liquid.

The compound may be administered to a subject by any desirable route, taking into consideration the specific condition for which it has been selected. The compound may, therefore, be delivered orally, by injection, i.e., transdermally, intravenously, subcutaneously, intramuscularly, intravenous, intra-arterial, intraperitoneal, intracavitary, or epiduraly, among others.

Although the compound may be administered alone, it may also be administered in the presence of one or more pharmaceutical carriers that are physiologically compatible. The carriers may be in dry or liquid form and must be pharmaceutically acceptable. Liquid pharmaceutical compositions are typically sterile solutions or suspensions.

When liquid carriers are utilized, they are desirably sterile liquids. Liquid carriers are typically utilized in preparing solutions, suspensions, emulsions, syrups and elixirs. In one embodiment, the compound is dissolved a liquid carrier. In another embodiment, the compound is suspended in a liquid carrier. One of skill in the art of formulations would be able to select a suitable liquid carrier, depending on the route of administration. In one embodiment, the liquid carrier includes, without limitation, water, organic solvents, oils, fats, or mixtures thereof. In another embodiment, the liquid carrier is water containing cellulose derivatives such as sodium carboxymethyl cellulose. In a further embodiment, the liquid carrier is water and/or dimethylsulfoxide. Examples of organic solvents include, without limitation, alcohols such as monohydric alcohols and polyhydric alcohols, e.g., glycols and their derivatives, among others. Examples of oils include, without limitation, fractionated coconut oil, arachis oil, corn oil, peanut oil, and sesame oil and oily esters such as ethyl oleate and isopropyl myristate.

Alternatively, the compound may be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, the solid carrier may also act as a flavoring agent, lubricant, solubilizer, suspending agent, filler, glidant, compression aid, binder, disintegrant, or encapsulating material. Suitable solid carriers include, without limitation, calcium phosphate, dicalcium phosphate, magnesium stearate, talc, starch, sugars (including, e.g., lactose and sucrose), cellulose (including, e.g., microcrystalline cellulose, methyl cellulose, sodium carboxymethyl cellulose), polyvinylpyrrolidine, low melting waxes, ion exchange resins, and kaolin. The solid carrier can contain other suitable excipients, including those described below.

Examples of excipients which may be combined with the compound include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, the excipients described in the "Handbook of Pharmaceutical Excipients", 5$^{th}$ Edition, Eds.: Rowe, Sheskey, and Owen, APhA Publications (Washington, D.C.), Dec. 14, 2005, which is incorporated herein by reference.

IV. Methods of using the Compound

Since the compounds described herein, and compositions containing same, contain $^{211}$At, they are radioactive and, thereby effective in radiotherapy applications in a patient.

The terms "patient" or "subject" as used herein refer to a mammalian animal. In one embodiment, the patient or subject is a human. In another embodiment, the patient or subject is a veterinary or farm animal, a domestic animal or pet, or animal normally used for clinical research. In still a further embodiment, the subject or patient has cancer. The subject or patient has either been recognized as having or at risk of having cancer.

As noted above, the compounds here are capable of modulating expression of the sigma-2-receptor/progesterone receptor membrane component 1 on a cell. In one embodiment, the cell is a cancer cell. The compounds and compositions prevent and/or reduce the proliferation of cancer cells thereby curing a patient or putting a patient in remission. Accordingly, the compounds discussed herein are useful in treating cancer by contacting the cells with a compound or composition discussed herein.

As used herein, "treatment" encompasses treatment of a subject clinically diagnosed as having a disease or medical condition. In one embodiment, the subject is treated and the disease or medical condition is eradicated, i.e., the subject is cured. As used herein, "prevention" encompasses prevention of symptoms in a subject who has been identified as at risk for the condition, but has not yet been diagnosed with the same and/or who has not yet presented any symptoms thereof.

The term "cancer" as used herein, refers to neoplastic cells in a patient which have abnormal cell group and invade or have the potential to invade one or more body parts of the patient. In one embodiment, the cancer is a neuroendocrine cancer. In another embodiment, the cancer is of the adrenal gland, appendix, bladder, blood, brain, bone, breast, bronchus, central nervous system, cervix, chest, colon, esophagus, eye, gallbladder, head, intestines, kidney, larynx, liver, lung, lymph nodes, mouth, neck, ovaries, pancreas, pharynx, pituitary, prostate, rectum, skin, stomach, testicles, throat, thymus, thyroid, uterus, urinary tract, or vagina, or is a leukemia. In a further embodiment, the cancer is breast cancer.

The compounds are also useful in sensitizing a cancer to treatment with a chemotherapeutic. In doing so, the compounds weaken some or all of the cancer cells to apoptosis by another chemotherapeutic agent or radiation. Alternatively, the compounds kill some of the cancer cells and a second chemotherapeutic or radiation may be utilized to kill the remaining cancer cells.

As described herein, a therapeutically or prophylactically effective amount of a compound is that amount of a compound which provides a sufficient amount of radiation. The sufficient amount of radiation may vary depending upon the formulation and route of delivery. In one embodiment, the amount (i.e., per unit) of the compound is that which does not exceed normal organ dose limits and delivers a tumoricidal dose to cancer cells. In one embodiment, the dose of the compound is dependent on the specific organ and cancer being treated. In another embodiment, the dose of the compound is the maximum dose tolerated by the patient. In a further embodiment, the compound delivers about 0.01 to about 100 mCi of radiation. In still another embodiment, the compound delivers about 0.05 to about 75 mCi of radiation. In still a further embodiment, the compound delivers about 0.1 to about 30 mCi of radiation. However, the effective amount to be used is subjectively determined by the attending physician and variables such as the size, age and response pattern of the patient.

These effective amounts may be provided on regular schedule, i.e., daily, weekly, monthly, or yearly basis or on an irregular schedule with varying administration days, weeks, months, etc. Alternatively, the effective amount to be administered may vary. In one embodiment, the effective amount for the first dose is higher than the effective amount for one or more of the subsequent doses. In another embodiment, the effective amount for the first dose is lower than the effective amount for one or more of the subsequent doses.

The methods described herein may be performed by administering a compound described herein via a combination therapy in prior to, concurrently with, or subsequent to another medication such as a chemotherapeutic. Such combination treatment may occur by administering compositions containing multiple active ingredients, as described above. However, also encompassed is a method of administration of chemotherapeutics in conjunction with a composition containing a compound described herein. In one embodiment, the compound and chemotherapeutic are administered to the patient by one or more selected routes of administration sequentially. In another embodiment, a chemotherapeutic agent is administered before treatment with a compound described herein. In another embodiment, a chemotherapeutic agent is administered after treatment with a compound described herein. In still another embodiment, a chemotherapeutic agent is administered during treatment with a compound described herein.

In one embodiment, a method of preventing or reducing proliferation of cancer cells is provided and includes contacting the cells with a compound or composition described herein.

In a further embodiment, a method of treating cancer in a patient is provided and includes administering a compound or composition described herein to the patient.

In another embodiment, a method of sensitizing cancer cells to a chemotherapeutic is provided and includes contacting the cells with a compound or composition described herein.

In yet a further embodiment, a method of administering radiotherapy to a patient in need thereof is provided and includes administering a compound or composition to the patient.

V. Kits Containing the Compound

Also provided herein are kits or packages of pharmaceutical formulations containing a compound or composition described herein. The kits may be organized to indicate a single formulation or combination of formulations to be taken at each desired time. The composition may also be sub-divided to contain appropriate quantities of the compound. For example, the unit dosage can be packaged compositions, e.g., packeted powders, vials, ampoules, pre-filled syringes or sachets containing liquids.

Suitably, the kit contains packaging or a container with the compound formulated for the desired delivery route. Suitably, the kit contains instructions on dosing and an insert regarding the compound. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the delivery device. Other suitable components to include in such kits will be readily apparent to one of skill in the art, taking into consideration the desired indication and the delivery route. The doses are repeated daily, weekly, or monthly, for a predetermined length of time or as prescribed.

The compound or composition described herein can be a single dose or for continuous or periodic discontinuous administration. For continuous administration, a package or kit can include the compound in each dosage unit (e.g., solution, lotion, tablet, pill, or other unit described above or utilized in drug delivery). When the compound is to be delivered with periodic discontinuation, a package or kit can include placebos during periods when the compound is not delivered. When varying concentrations of a composition, of the components of the composition, or of relative ratios of the compound or other agents within a composition over time is desired, a package or kit may contain a sequence of dosage units, so varying.

A number of packages or kits are known in the art for the use in dispensing pharmaceutical agents for oral use. In one embodiment, the package has indicators for each period. In another embodiment, the package is a labeled blister package, dial dispenser package, or bottle.

The packaging means of a kit may itself be geared for administration, such as an inhalant, syringe, pipette, eye dropper, or other such like apparatus, from which the formulation may be applied to an infected area of the body, such as the lungs, injected into a subject, or even applied to and mixed with the other components of the kit.

The compound or composition of these kits also may be provided in dried or lyophilized forms. When reagents or components are provided as a dried form, reconstitution generally is by the addition of a suitable solvent. It is envisioned that the solvent also may be provided in another packaging means.

The kits may include a means for containing the vials in close confinement for commercial sale such as, e.g., injection or blow-molded plastic containers into which the desired vials are retained.

Irrespective of the number or type of packages, the kits also may include, or be packaged with a separate instrument for assisting with the injection/administration or placement of the ultimate complex composition within the body of an animal. Such an instrument may be an inhalant, syringe, pipette, forceps, measuring spoon, eye dropper or any such medically approved delivery means. Other instrumentation includes devices that permit the reading or monitoring of reactions in vitro.

In one embodiment, a pharmaceutical kit is provided and contains a compound of formula (I). The compound may be in the presence or absence of one or more of the carriers or excipients described above. The kit may optionally contain a chemotherapeutic and/or instructions for administering the chemotherapeutic and the compound to a subject having cancer.

In a further embodiment, a pharmaceutical kit is provided and contains a chemotherapeutic in a first dosage unit, one or more of a compound selected from those described herein in a second dosage unit, and one or more of the carriers or excipients described above in a third dosage unit. The kit may optionally contain instructions for administering the chemotherapeutic and/or compound to a subject having cancer.

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

EXAMPLES

Example 1: $^{211}$At Production and Distillation $^{211}$At was produced via the nuclear reaction $^{209}$Bi($\alpha$,2n)$^{211}$At, on a Japan Steel Works BC3015 cyclotron using external solid target (8) positioned perpendicular to the beam line. The solid target (8) diameter was 1.6 cm and consisted of a 75 μm thick $^{209}$Bi layer backed by 1100 aluminum alloy. The beam energy was degraded from 30 to 28.4 MeV by using a 75 μm thick aluminum degrader foil attached directly to the $^{209}$Bi surface. A defocused beam profile was used to spread the beam across a larger surface area to mitigate pinpoint heating and subsequent melting due to the poor thermal properties of $^{209}$Bi and the perpendicular incident beam angle.

Figure 2:
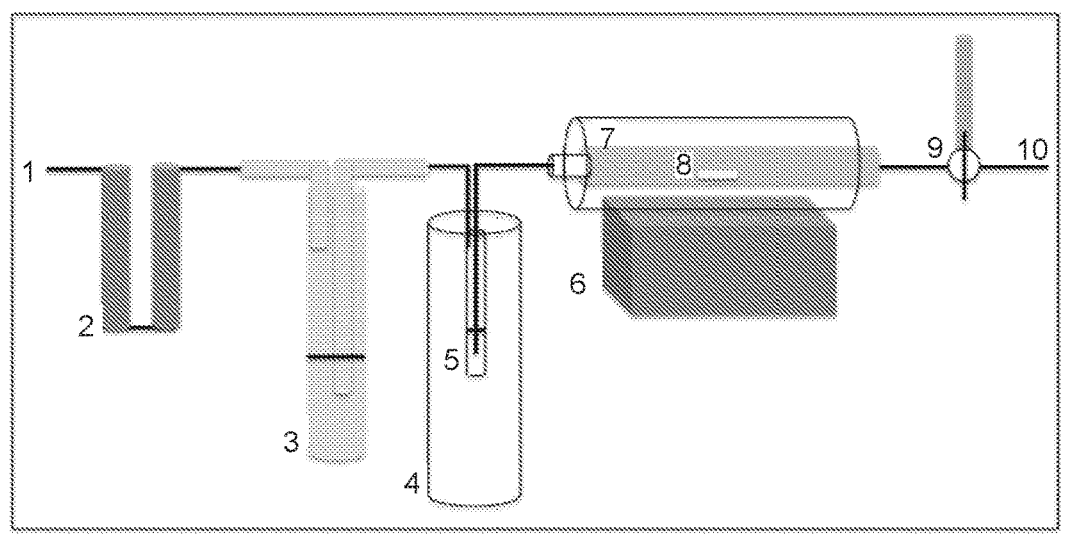
FIG. 2 is a schematic of an apparatus for the dry distillation of $^{211}$Astatine.

Dry distillation was performed to isolate $^{211}$At from the solid target (8). See, FIG. 2. The foil was removed from solid target (8) and the backing with $^{209}$Bi/$^{211}$At layer was cleaned to remove any thermal paste using alcohol wipes, hexane and acetone. The cleaned and dried target was placed in a quartz boat and was positioned inside the quartz furnace tube (7). The entire distillation apparatus was assembled and vacuum initiated through vacuum outlet (1). The apparatus also contained a vacuum trap (3) to trap extraneous liquids, a charcoal trap (2) to prevent volatilized $^{211}$At being discharged, and a liquid NaOH trap (5) to collect the $^{211}$At. Once the entire system was evacuated, a slow argon gas stream was turned on from argon inlet (10) along with furnace (6). A vent (9) was attached to the argon inlet (10) to for modulation of the pressure. Furnace (6), which is adjacent to the quartz furnace tube, was adjusted to a maximum temperature of 700° C. and was held for 10 minutes. Radioactivity in the collection vessel (5) was monitored in real time with dose calibrator (4; Capintec, Inc, Ramsey N.J.) using the $^{133}$Xe setting and a 2.3 conversion factor to calculate $^{211}$At radioactivity.

$^{211}$At production yields up to 340.4 MBq were achieved and are presented in Table 1. Dry distillation of $^{211}$At resulted in decay corrected recovery yields from 50-89%, median=60% (Table 1). Monitoring the collection vessel radioactivity in real time provided instant feedback of the distillation process and helped adequately fine tune the parameters of temperature and argon flow. The entire distillation process lasted about 45 min.

TABLE 1

$^{211}$At production and distillation - distillation yield presented as recovered radioactivity from measured solid target.

| Average Current (μA) | μA * h | Production Yield (MBq/μA * h) | Distillation Yield (MBq) | Decay Corrected Distillation Yield (%) |
|---|---|---|---|---|
| 10 | 30.1 | 10.4 | 238 | 89 |
| 10 | 20 | 9.8 | 107 | 61 |
| 6.8 | 20.1 | 9.2 | 104 | 64 |

TABLE 1-continued

[211At] production and distillation - distillation yield presented as recovered radioactivity from measured solid target.

| Average Current (μA) | μA * h | Production Yield (MBq/μA * h) | Distillation Yield (MBq) | Decay Corrected Distillation Yield (%) |
|---|---|---|---|---|
| 9.9 | 13.3 | 8.6 | 70 | 66 |
| 7.5 | 16.95 | 7.5 | 85 | 76 |
| 9 | 45.4 | 8.7 | 196 | 58 |

Example 2: Precursor and Standard Synthesis

The precursor, i.e., N-(4-(6,7-dimethoxy-3,4-dihydroisoquinolin-2(1H)-yl)butyl)-2,3-dimethoxy-5-(tributylstannyl)benzamide, and standard, i.e., 5-iodo-N-(4-(6,7-dimethoxy-3,4-dihydroisoquinolin-2(1H)-yl)butyl)-2,3-dimethoxybenzamide, were synthesized as described in Hou, "Characterization of a novel iodinated sigma-2 receptor ligand as a cell proliferation marker," Nuclear medicine and biology, 2006; 33(2):203-209 and Tu, "Fluorine-18-labeled benzamide analogues for imaging the sigma-2 receptor status of solid tumors with positron emission tomography," Journal of Medicinal Chemistry, 2007; 50(14):3194-3204, which documents are incorporated by reference.

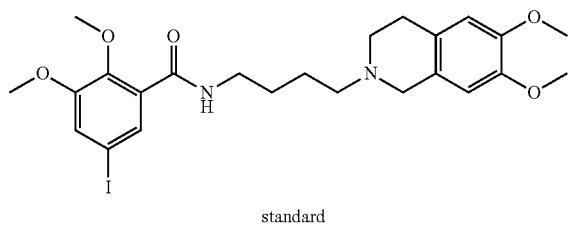

standard

Example 3: Synthesis of $^{211}$At—N-(6,7-dimethoxy-3,4-dihydroisoquinolin-2(1H)-yl)butyl)-2,3-dimethoxybenzamide The title compound was synthesized by electrophilic radioastatodestannylation. Briefly, 0.1 M NaOH/$^{211}$At (1 mL) was added to precursor (100 μg), followed by 3:1, glacial acetic acid:hydrogen peroxide (100 μg). The reaction was vortexed periodically over 20 minutes, then quenched with ammonium formate (AMF; 3.5 mL) pH 4.5 and purified by High Performance Liquid Chomatography (HPLC) on a reversed phase C-18 Phenomenex® column (250×10 mm, 5 μM). Isocratic mobile phase of 30:70 acetonitrile: 0.1 M AMF pH 4.5 was used with UV wavelength of 288 nm and flow rate of 4 mL/min. The radioactive peak was collected at 23 minutes, diluted to 50 mL with water, and then concentrated on C-18 light Sep-Pak® cartridge (Waters, Milford Mass.). Product was eluted from cartridge using 200 proof ethanol in a volume of 100 μL. Quality control was performed using the same mobile phase as above on a reversed phase C-18 Agilent Zorbax® (4.6×150 mm, 5 μM) analytical column. Co-injection of the standard was used to identify $^{211}$At—N-(6,7-dimethoxy-3,4-dihydroisoquinolin-2(1H)-yl)butyl)-2,3-dimethoxybenzamide. There was no UV mass observed associated with this product so the specific activity of the title compound was assumed to be the same as the theoretical for $^{211}$At (435,000 curies/mmol).

$^{211}$At—N-(6,7-dimethoxy-3,4-dihydroisoquinolin-2(1H)-yl)butyl)-2,3-dimethoxybenzamide was synthesized with average recovery yield of 70% and is highly comparable to similar iodination chemistry. Radiochemical purity was >95% with no observable UV mass. Co-injection of the title compound and non-radioactive standard resulted in UV and radioactive peak elution at similar retention times.

Radiosynthesis of $^{211}$At—N-(6,7-dimethoxy-3,4-dihydroisoquinolin-2(1H)-yl)butyl)-2,3-dimethoxybenzamide was reproducible with high radiochemical purity.

Example 4: Further Compounds

The compounds of FIG. 1 may be prepared using the synthetic steps of Example 3 and U.S. Pat. No. 7,390,902 which is incorporated by reference.

Example 5: In Vitro Binding Studies $^{211}$At—N-(6,7-dimethoxy-3,4-dihydroisoquinolin-2(1H)-yl)butyl)-2,3-dimethoxybenzamide was evaluated in MDA-MB-231 breast cancer cells (ATCC-HTB-26) known to have high sigma-2 receptor density and compared with the well-characterized sigma-2 selective ligand standard. MDA-MB-231 were cultured in Minimum Essential Media (MEM) with added nutrients, 10% fetal bovine serum (FBS) and 1% penicillin/streptomycin at 5% $CO_2$ and 37° C. Twenty-four hours before assay cells were plated at 50,000 cell/well in 96-well format. Two solutions of freshly synthesized radioligand were diluted to a concentration of approximately 2,000 cpm/μL in phosphate buffered saline with calcium and magnesium (PBS w/ $Ca^{2+}$ and $Mg^{2+}$), with and without non-radioactive 100 μM of the standard to determine non-specific binding. At the time of assay, culture media was removed and $^{211}$At—N-(6,7-dimethoxy-3,4-dihydroisoquinolin-2(1H)-yl)butyl)-2,3-dimethoxybenzamide or $^{211}$At—N-(6,7-dimethoxy-3,4-dihydroisoquinolin-2(1H)-yl)butyl)-2,3-dimethoxybenzamide+100 μM of the standard was added to the wells. Total volume of treatment in each well was 50 μL. PBS w/ $Ca^{2+}$ and $Mg^{2+}$ without substrate was added to the last row of wells and was used for protein quantification at the end of the experiment. Treatment was removed at time points over the course of 2 h (n=4/time point). At each time of treatment removal, wells were washed with PBS×3. At the end of the experiment wells were counted on an automatic gamma counter using a custom protocol with an energy window of 70-110 KeV (Wizard™ 2470, Perkin Elmer, Waltham Mass.). Protein quantification was performed using a modified Lowry method. Independent experiments were repeated in triplicate. One-phase association kinetics were modeled using Prism™ software version 6.0 (La Holla, Calif.).

Figure 3:
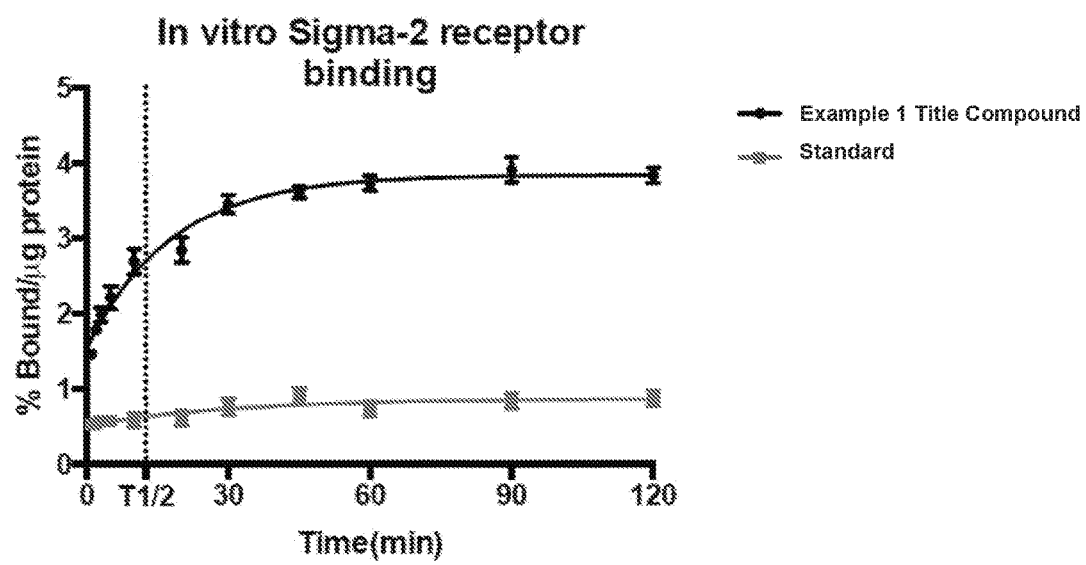
FIG. 3 is a graph illustrating in vitro sigma-2 receptor binding of $^{211}$At—N-(6,7-dimethoxy-3,4-dihydroisoquinolin-2(1H)-yl)butyl)-2,3-dimethoxybenzamide alone (●) or in combination with a standard (※) to human-derived breast cancer cells. Error bars are presented as the standard of error measure (SEM). The time of half-maximal binding ($T_{1/2}$) is represented by a dashed line.

Live cellular binding studies with $^{211}$At—N-(6,7-dimethoxy-3,4-dihydroisoquinolin-2(1H)-yl)butyl)-2,3-dimethoxybenzamide in MDA-MB-231 cells resulted in sigma-2 binding and demonstrated retained affinity to tumor cells. Fast kinetics were observed with 50% maximal binding occurring at 12.51 min. Selective sigma-2 competitive inhibition was shown with an 80% reduction in total binding of $^{211}$At—N-(6,7-dimethoxy-3,4-dihydroisoquinolin-2(1H)-yl)butyl)-2,3-dimethoxybenzamide through the addition of the standard. FIG. 3 represents data from 3 independent experiments. Average protein quantification for experiments was 7.4±0.75 μg.

Example 6: In Vivo Biodistribution

Tumors were grown by subcutaneously injecting 1×10$^6$ EMT-6 mouse breast cancer cells (ATCC #CRL-2755) into the flanks of female BALB/c mice (Taconic). Tumors were an appropriate size of approximately 200 mm³ after 14 days of growth. On the day of experiment 10 µCi of newly synthesized ²¹¹At—N-(6,7-dimethoxy-3,4-dihydroisoquinolin-2(1H)-yl)butyl)-2,3-dimethoxybenzamide in saline (ethanol<5%) was administered intravenously to mice under isoflurane anesthesia. Mice were sacrificed by cervical dislocation followed by immediate cardiac puncture post administration at time points of 5 min, 1, 2, 4, 8, and 24 h (n=4 mice/time point). Tissue harvested included; blood, heart, muscle, lung, kidney, pancreas, spleen, liver, skin, brain, thyroid, stomach and EMT-6 tumor. Tissues were weighed and counted on an automatic gamma counter as previously described. All animal experiments were conducted under IACUC-approved protocols compliant with University of Pennsylvania guidelines for the care and use of research animals.

Biodistribution was evaluated over 24 h showing high initial kidney uptake at 5 min (47.7% ID/g) with rapid clearance over 1 h (5.83% ID/g). Similar results were also seen, although to a lesser extent, in the liver. Tumor accumulation of ²¹¹At—N-(6,7-dimethoxy-3,4-dihydroisoquinolin-2(1H)-yl)butyl)-2,3-dimethoxybenzamide remained above 4% ID/g from 1 h to at least 8 h. At 24 h, the majority of decay corrected radioactivity was cleared from all tissues. Considerable uptake was noted in the stomach, thyroid and pancreas. High uptake of radioactivity in the stomach and thyroid might be due to in vivo deastatination. Future metabolite studies are needed to verify this and define what percentage of deastatination occurs. The high uptake in the pancreas is expected due to the high expression of the sigma-2 receptor. Biodistribution data is presented in Table 2 and tumor:muscle/blood ratios are presented in FIG. 4.

TABLE 2

| Decay corrected biodistribution data presented as percent injected dose/gram (% ID/g). | | | | | | |
|---|---|---|---|---|---|---|
|  | 5 min (N = 4) | 1 h (N = 4) | 2 h (N = 4) | 4 h (N = 4) | 8 h (N = 4) | 24 h (N = 4) |
| Blood | 4.06 ± 0.19 | 2.12 ± 0.15 | 2.43 ± 0.82 | 1.64 ± 0.11 | 1.82 ± 0.10 | 0.44 ± 0.10 |
| Heart | 10.2 ± 0.82 | 5.16 ± 1.21 | 4.70 ± 0.31 | 3.54 ± 0.17 | 4.01 ± 0.29 | 1.14 ± 0.27 |
| Muscle | 0.69 ± 0.16 | 1.24 ± 0.18 | 1.15 ± 0.07 | 0.56 ± 0.03 | 0.61 ± 0.04 | 0.19 ± 0.01 |
| Lung | 20.2 ± 1.39 | 7.14 ± 1.03 | 6.42 ± 0.39 | 5.74 ± 0.53 | 6.23 ± 0.57 | 2.21 ± 0.40 |
| Kidney | 47.7 ± 2.32 | 5.83 ± 0.53 | 5.59 ± 0.35 | 2.97 ± 0.13 | 3.24 ± 0.21 | 1.05 ± 0.23 |
| Pancreas | 8.81 ± 1.21 | 18.1 ± 1.60 | 18.0 ± 1.65 | 26.3 ± 2.11 | 21.1 ± 2.35 | 5.78 ± 0.89 |
| Spleen | 8.41 ± 2.67 | 13.2 ± 2.76 | 12.0 ± 1.47 | 7.59 ± 0.49 | 7.49 ± 1.38 | 2.14 ± 1.02 |
| Liver | 18.1 ± 2.11 | 6.39 ± 3.27 | 4.63 ± 1.01 | 1.87 ± 0.17 | 1.86 ± 0.19 | 0.59 ± 0.20 |
| Skin | 0.58 ± 0.05 | 2.30 ± 0.23 | 2.66 ± 0.30 | 1.79 ± 0.15 | 2.10 ± 0.42 | 0.85 ± 0.08 |
| Brain | 1.95 ± 0.14 | 0.46 ± 0.08 | 0.39 ± 0.01 | 0.21 ± 0.02 | 0.25 ± 0.02 | 0.07 ± 0.02 |
| Thyroid | 5.87 ± 0.85 | 11.6 ± 1.01 | 18.3 ± 6.12 | 14.0 ± 4.26 | 13.3 ± 2.96 | 4.87 ± 1.15 |
| Stomach | 5.87 ± 1.12 | 15.9 ± 2.53 | 16.3 ± 2.29 | 19.7 ± 1.79 | 28.2 ± 7.21 | 9.88 ± 1.62 |
| Tumor | 0.74 ± 0.07 | 4.40 ± 0.15 | 4.93 ± 0.78 | 5.05 ± 0.68 | 5.11 ± 0.09 | 1.34 ± 0.37 |

Figure 4:
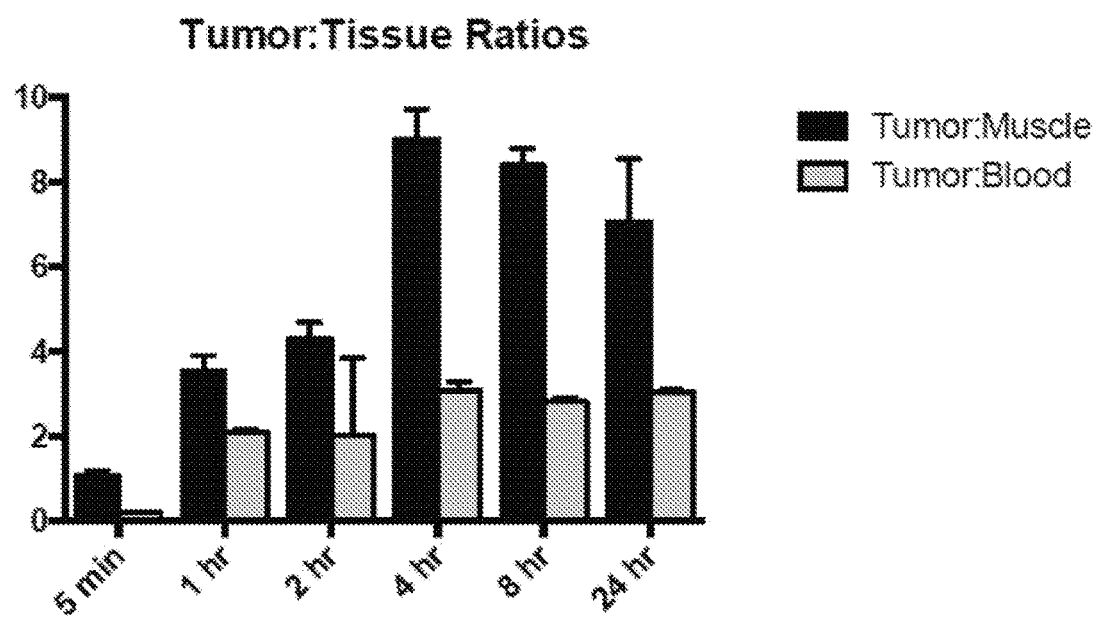
FIG. 4 is a bar graph illustrating the tumor:muscle (■) and tumor:blood ratios (※) over a period of 24 h. Error bars are represented as standard deviation (SD).

The results show retention of radioactivity in the tumor from 1-8 h post administration. The iodinated sigma-2 ligand standard was shown to have tumor clearance by 4 h with a lower tumor uptake of 2% ID/g. Tumor retention of ²¹¹At—N-(6,7-dimethoxy-3,4-dihydroisoquinolin-2(1H)-yl)butyl)-2,3-dimethoxybenzamide is highly desirable as a therapeutic and provides a tumor residence time approximately equal to the half-life of ²¹¹At ($t_{1/2}$=7.21 h) providing at least 50% of total possible radiation dose to the tumor before washout. The results also illustrate a maximal tumor to muscle ratio of 9.02 at 4 h (FIG. 4).

In vivo deastatination is the suspected cause of off-target localization in the thyroid and stomach. It is hypothesized that off-target localization might be due to sigma-2 receptor expression in the thyroid and stomach. The pancreas also had an appreciable amount of radioactivity localized. It is hypothesized that there is a known high expression of sigma-2 receptors on endocrine glands. At 24 h, most of the decay corrected ²¹¹At—N-(6,7-dimethoxy-3,4-dihydroisoquinolin-2(1H)-yl)butyl)-2,3-dimethoxybenzamide was cleared from all tissues.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed is:

1. A compound of formula (I):

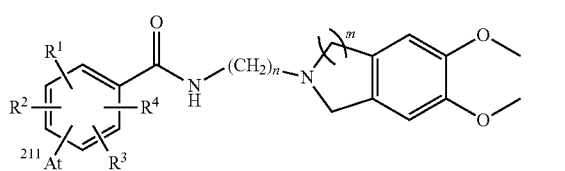

wherein:
  m is 1 or 2;
  n is 1 to 10;
  $R_1$ to $R^4$ are at the 2-, 3-, 4-, 5-, or 6-position of the benzene ring and, independently, H, $C_1$ to $C_6$ alkyl, $C_1$ to $C_6$ alkoxy, $C_1$ to $C_6$ haloalkyl, halogen, $C_1$ to $C_6$ fluoroalkoxy, $C_1$ to $C_6$ thioalkyl, $C_1$ to $C_6$ thio-haloalkyl, $NH_2$, $C_1$ to $C_6$ aminoalkyl, or —$(OCH_2CH_2)_q$—F;
  q is 2 to 6;
  or $R^1$ and $R^2$; $R^2$ and $R^3$; or $R^3$ and $R^4$ together form a 5- or 6-membered benzene ring substituted with H or 1 to 4 $R^5$;
  $^{211}$At is at the 2-, 3-, 4-, 5- or 6-position of the benzene ring; and
  $R^5$ is H, $C_1$ to $C_6$ alkyl, $C_1$ to $C_6$ alkoxy, $C_1$ to $C_6$ haloalkyl, halogen, $C_1$ to $C_6$ fluoroalkoxy, $C_1$ to $C_6$ thioalkyl, $C_1$ to $C_6$ thio-haloalkyl, $NH_2$, $C_1$ to $C_6$ aminoalkyl, or —$(OCH_2CH_2)_q$—F;
  with the proviso that two of $R^1$-$R^4$ and $^{211}$At do not occupy the same position on said benzene ring;
or a pharmaceutically acceptable salt or prodrug thereof.

2. The compound of claim 1, of formula (II):

(II)

3. The compound of claim 1, wherein said halogen is a radioactive isotope.

4. The compound of claim 1, wherein $R^1$ is $C_1$ to $C_6$ fluoroalkoxy.

5. The compound of claim 3, wherein $R^1$ is $O(CH_2)_pF$ and p is 1 to 10.

6. The compound of claim 1, wherein n is 2 to 4.

7. The compound of claim 1, of formula (III):

(III)

8. The compound of claim 1, of formula (IV):

(IV)

9. The compound of claim 1, of formula (V):

(V)

10. The compound of claim 1, of formula (VI):

(VI)

11. The compound of claim 1, of formula (VII):

(VII)

12. The compound of claim 1, of formula (VIII):

(VIII)

13. The compound of claim 1, which is:

14. A compound which is 5-($^{211}$astatine)-N-(4-(6,7-dimethoxy-3,4-dihydroisoquinolin-2(1H)-yl)butyl)-2,3-dimethoxybenzamide, derivative, salt, or prodrug thereof.

15. A composition comprising a compound of claim 1 and a pharmaceutically acceptable carrier or diluent.

16. A method of
reducing proliferation of cancer cells, or
sensitizing cancer cells to a chemotherapeutic;
said method comprising contacting said cells with a compound of claim 1.

17. The method of claim 16, further comprising administering radiation to said cells.

18. A method of treating cancer in a patient sensitizing a patient's cancer cells to a chemotherapeutic or administering radiotherapy to a patient, said method comprising administering a compound of claim 1 to said patient.

19. The method of claim 18, wherein said cancer is a neuroendocrine cancer.

20. The method of claim 18, wherein said cancer is of the prostate, head, neck, eye, mouth, throat, esophagus, bronchus, larynx, pharynx, chest, bone, lung, colon, rectum, stomach, bladder, uterus, cervix, breast, ovaries, vagina, testicles, thyroid, blood, lymph nodes, kidney, liver, intestines, pancreas, brain, central nervous system, adrenal gland, neuroendocrine, or skin or a leukemia.

21. The method of claim 18, further comprising administering radiation to said patient.

22. The method of claim 18, wherein said compound is administered to said patient through intravenous, intraarterial, intraperitoneal or intracavitary injection.

23. The method of claim 18, comprising administering an amount of said compound having from about 0.01 to about 100 Curies of radiation.

* * * * *

UNITED STATES PATENT AND TRADEMARK OFFICE
CERTIFICATE OF CORRECTION

PATENT NO. : 10,457,642 B2
APPLICATION NO. : 15/571055
DATED : October 29, 2019
INVENTOR(S) : Pryma et al.

Page 1 of 1

It is certified that error appears in the above-identified patent and that said Letters Patent is hereby corrected as shown below:

In the Specification

Under Heading "Background", Column 1, Line 66, replace "F-fluoromethoxy)-5-" with
-- F-fluoroethoxy)-5- --

Signed and Sealed this
Seventeenth Day of March, 2020

Andrei Iancu
*Director of the United States Patent and Trademark Office*